(12) United States Patent
Li (10) Patent No.: US 11,292,753 B2
(45) Date of Patent: Apr. 5, 2022

(54) METHOD FOR ALCOHOL UPGRADING TO JET, DIESEL, GASOLINE, AND VALUABLE CO-PRODUCTS

(71) Applicant: UT-Battelle, LLC, Oak Ridge, TN (US)

(72) Inventor: Zhenglong Li, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 17/083,437

(22) Filed: Oct. 29, 2020

(65) Prior Publication Data

US 2021/0130257 A1    May 6, 2021

Related U.S. Application Data

(60) Provisional application No. 62/927,792, filed on Oct. 30, 2019.

(51) Int. Cl.
  *C07C 1/24* (2006.01)
  *F23K 5/08* (2006.01)
  (Continued)

(52) U.S. Cl.
  CPC ............... *C07C 1/24* (2013.01); *C07C 2/08* (2013.01); *C07C 5/03* (2013.01); *F23K 5/08* (2013.01);
  (Continued)

(58) Field of Classification Search
  CPC .... C07C 1/20; C07C 1/24; C07C 2/08; C07C 5/03; C07C 5/333; C07C 5/41;
  (Continued)

(56) References Cited

U.S. PATENT DOCUMENTS 5,215,648 A    6/1993  Zones et al.
9,181,493 B2  11/2015  Narula et al.
(Continued)

FOREIGN PATENT DOCUMENTS

WO    2004/071656 A1    8/2004
WO    2014/074988 A1    5/2014

OTHER PUBLICATIONS

Na et al. (J. Am. Chem. Soc. 2010, 132, 4169-4177) (Year: 2010).*
(Continued)

*Primary Examiner* — Youngsul Jeong
*Assistant Examiner* — Jason Y Chong
(74) *Attorney, Agent, or Firm* — Scully, Scott, Murphy & Presser, P.C.

(57) ABSTRACT

A method for converting an alcohol to a jet-diesel hydrocarbon fraction, comprising contacting the alcohol with a pillared two-dimensional zeolite catalyst at a temperature of at least 200° C. and up to 500° C. to convert the alcohol to hydrocarbons comprising: (a) a first mixed olefin fraction containing a mixture of $C_2$-$C_5$ olefins; (b) a first paraffin fraction containing $C_3$-$C_5$ paraffins; and (c) a gasoline fraction containing $C_6^+$ hydrocarbons; and the conversion of the alcohol is energy neutral or exothermic. The first mixed olefin fraction may be subjected to an oligomerization process to result in a second paraffin fraction containing $C_3$-$C_6$ paraffins along with a $C_7^+$ partially unsaturated fraction, and the first and second paraffin fractions combined into a total $C_3$-$C_6$ paraffin fraction, which can in turn be subjected to a dehydrogenation or aromatization process with hydrogen gas as byproduct, and the hydrogen gas recycled for use in producing the jet-diesel fraction.

22 Claims, 3 Drawing Sheets (51) Int. Cl.
*C07C 5/03* (2006.01)
*C07C 2/08* (2006.01)
(52) U.S. Cl.
CPC ...... *C07C 2529/05* (2013.01); *C07C 2529/40* (2013.01)
(58) Field of Classification Search
CPC ... C07C 2529/05; C07C 2529/40; F23K 5/08; Y02P 20/52; C10G 57/02; C10G 69/00; C10G 69/126; C10G 69/14; C10G 3/49
See application file for complete search history.

(56) References Cited

U.S. PATENT DOCUMENTS

| | | | |
|---|---|---|---|
| 9,278,892 | B2 | 3/2016 | Narula et al. |
| 9,434,658 | B2 | 9/2016 | Narula et al. |
| 9,533,921 | B2* | 1/2017 | Narula ............... B01J 29/061 |
| 9,938,467 | B2 | 4/2018 | Narula et al. |
| 10,300,474 | B2 | 5/2019 | Li |
| 10,696,606 | B2 | 6/2020 | Narula et al. |
| 2013/0059722 | A1* | 3/2013 | Tsapatsis ............... C01B 39/40 502/4 |
| 2016/0257624 | A1* | 9/2016 | Schoenfeldt ........... B01J 35/002 |
| 2016/0312134 | A1 | 10/2016 | Fichtl et al. |
| 2019/0344252 | A1* | 11/2019 | Cho ..................... C07C 51/42 |
| 2020/0048170 | A1 | 2/2020 | Li |

OTHER PUBLICATIONS

Bhan, A., et al., "Propane Aromatization over HZSM-5 and Ga/HZSM-5 Catalysts", Catalysis Reviews, accepted Apr. 28, 2007, Published online Feb. 4, 2008, pp. 19-151, 50.

International Search Report dated Jan. 28, 2021 together with the Written Opinion received in International Application No. PCT/US 20/57822, 15 pages.

Lacarriere, A., et al., "Distillate-Range Products from Non-Oil-Based Sources by Catalytic Cascade Reactions", ChemSusChem 2012, Published online Jul. 3, 2012, pp. 1787-1792, 5.

Nawaz, Z., "Light alkane dehydrogenation to light olefin technologies: a comprehensive review", Rev Chem Eng 2015; aop, accepted Jun. 11, 2015, pp. 1-24.

Xiang, Y., et al., "Progress and prospects in catalytic ethane aromatization", Catalysis Science & Technology, The Royal Society of Chemistry 2018, Accepted Feb. 8, 2018, Published on Feb. 14, 2018, 17 pages.

* cited by examiner

METHOD FOR ALCOHOL UPGRADING TO JET, DIESEL, GASOLINE, AND VALUABLE CO-PRODUCTS

CROSS REFERENCE TO RELATED APPLICATION

The present application claims benefit of U.S. Provisional Application No. 62/927,792, filed on Oct. 30, 2019, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates, generally, to the catalytic conversion of alcohols to hydrocarbons, and more particularly, to zeolite-based catalytic methods for conversion of alcohols, such as ethanol, to olefins, paraffins, and gasoline fractions.

BACKGROUND OF THE INVENTION

As part of a continuing effort in finding more cost-effective, environmentally friendly, and independent solutions to fuel production and consumption, the conversion of ethanol and other alcohols to hydrocarbons has become an active field of study. Ethanol, in particular, is of particular interest as an alcohol feedstock because it has the potential to be made in large quantity by renewable means (e.g., fermentation of biomass). However, several hurdles need to be overcome before such a process can become industrially feasible for producing olefins and hydrocarbon blendstocks of substantial equivalence to jet fuel, gasoline and other petrochemical fuels.

A few ethanol conversion technologies for jet fuel production are currently available. The first technology is via ethanol dehydration, oligomerization, and hydrogenation. This technology requires significant energy input due to the endothermic dehydration reaction. The carbon efficiency for producing the desired jet fuel is still very low, and the ethylene oligomerization step is usually very costly. Also, external hydrogen is employed for the hydrogenation step. The second approach is to convert ethanol to isobutylene via a mixed oxide catalyst, followed by oligomerization and hydrogenation. A major limitation of the foregoing process is the low carbon efficiency due to a substantial amount of carbon dioxide formation. The foregoing approach also employs an external hydrogen supply. The third technology is converting alcohols to hydrocarbon blendstock (aromatics rich) via one or multiple steps using metal exchanged zeolites. However, the foregoing technology produces a limited jet/diesel fraction. There would be a significant benefit in a process that could produce olefins (and ultimately, a synthetic fossil fuel) from alcohols with a higher carbon efficiency, greater overall energy efficiency, and with less or no reliance on an external hydrogen supply.

SUMMARY OF THE INVENTION

The present disclosure is directed to an improved method for converting an alcohol to a jet-diesel hydrocarbon fraction. The method is useful for converting aqueous alcohols into jet, diesel, gasoline and valuable co-products (benzene, toluene and polymer grade p-xylene, olefins). The method described herein produces the jet-diesel hydrocarbon fraction with substantial carbon efficiency and overall energy efficiency and with substantially less or no reliance on an external hydrogen supply. To improve the energy efficiency, the method employs a first step of converting the alcohol to an initial mixed hydrocarbon blend, which includes a mixed olefin fraction, paraffin fraction, and gasoline fraction, under specialized conditions that render the conversion process as an energy neutral or slightly exothermic process. To lessen the reliance on an external hydrogen supply, the method diverts hydrogen gas produced in a paraffin dehydrogenation step to hydrogenation of a $C_7^+$ partially unsaturated fraction to produce the jet-diesel hydrocarbon fraction. By the present method, the majority of the carbon is advantageously converted to non-aromatic jet/diesel, gasoline and valuable coproducts. Moreover, the first step can be tuned between slightly exothermic and neutral, which greatly reduces the external energy supply and facilitates scale-up.

More particularly, in the first step, one or more alcohols are converted to $C_2$-$C_5$ hydrocarbons (olefin-rich fraction along with $C_3$-$C_5$ paraffins) and gasoline fraction ($C_6^+$) by contacting the one or more alcohols with a pillared two-dimensional zeolite catalyst having an MFI structure, typically with higher Si/Al ratio (>20). The reaction temperature is generally in the range of 200 to 500° C. In some embodiments, the weight hourly space velocity can be increased to 10, 15, or 20 h$^{-1}$. The yield of $C_2$-$C_6$ mixed olefins can be achieved up to, for example, 70, 80, 85, or 90 wt %. The yield of gasoline fraction is generally in the range of 5-17 wt %. An oligomerization process on the olefin-rich fraction results in production of $C_3$-$C_6$ paraffins, which can be easily separated from the heavier oligomers. The oligomerization process also produces a $C_7^+$ partially unsaturated (oligomeric) fraction. The $C_3$-$C_6$ paraffins, typically containing 2-5% propane, 7-13% butanes and 1-4% $C_5$ and $C_6$ paraffins, can be converted to polymer grade p-xylene, benzene and toluene with surface-modified ZSM-5. Hydrogen gas is produced as a byproduct, which can be used in a hydrogenation step for jet/diesel production. An alternative approach can be used to convert $C_3$-$C_5$ paraffins into $C_3$-$C_5$ mixed olefins and hydrogen gas (as a byproduct) via dehydrogenation. If desired, the $C_3$-$C_5$ olefins can be combined with the $C_2$-$C_6$ olefins to produce a jet-diesel hydrocarbon fraction, or used for polymer production after proper separation. Notably, the $C_7^+$ partially unsaturated (oligomeric) fraction can be hydrogenated, using the above produced hydrogen gas (i.e., as recycled from the paraffin dehydrogenation or aromatization process), to produce the jet-diesel hydrocarbon fraction.

Figure 1:
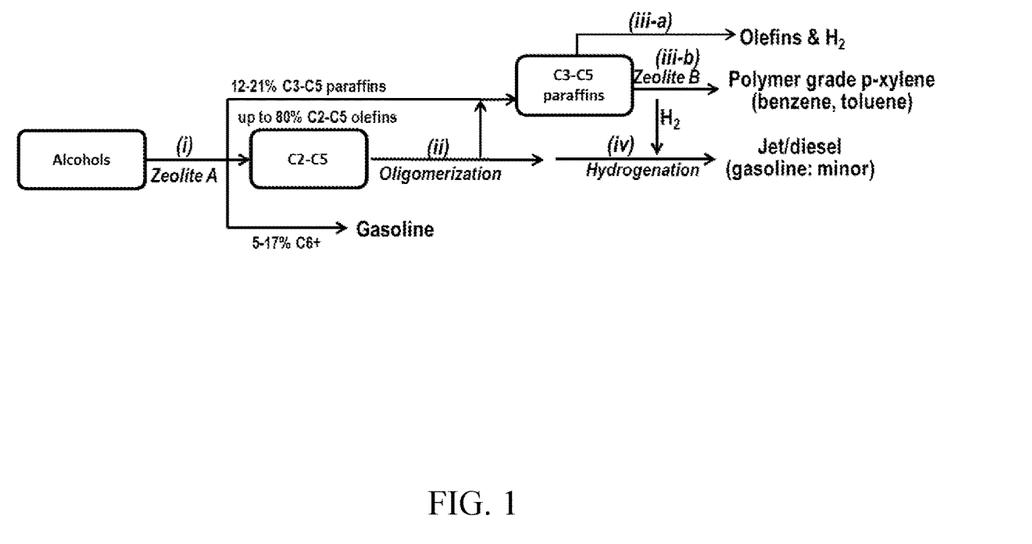
FIG. 1. A general schematic of the presently described process for producing jet/diesel and gasoline fractions from alcohol.

An overview schematic of the process is provided in FIG. 1. As depicted in FIG. 1, the presently described method includes the following steps for converting an alcohol to a jet-diesel hydrocarbon fraction: (i) contacting the alcohol with a pillared two-dimensional zeolite catalyst having an MFI structure at a temperature of at least 200° C. and up to 500° C. to result in conversion of said alcohol to said hydrocarbons, wherein said hydrocarbons comprise: (a) a first mixed olefin fraction containing a mixture of $C_2$-$C_5$ olefins; (b) a first paraffin fraction containing $C_3$-$C_5$ paraffins; and (c) a gasoline fraction containing $C_6^+$ hydrocarbons; wherein the first mixed olefin fraction accounts for at least 25 carbon mol % of total fractions (a)-(c), and the conversion of the alcohol is energy neutral or exothermic; (ii) subjecting said first mixed olefin fraction to an oligomerization process in which the first mixed olefin fraction is contacted with an oligomerization catalyst at a temperature of at least 40° C. and up to 300° C. to result in a second paraffin fraction containing $C_3$-$C_6$ paraffins along with a $C_7^+$ partially unsaturated fraction, and combining said first and second paraffin fractions to result in a total $C_3$-$C_6$ paraffin fraction; (iii) subjecting at least a portion of said total $C_3$-$C_6$ paraffin fraction to one or both of the following processes: (iii-a) a dehydrogenation process in which at least a portion of said total $C_3$-$C_6$ paraffin fraction is contacted with a noble metal-containing or metal oxide-containing catalyst at a temperature of at least 500° C. and up to 600° C. to form a second mixed olefin fraction containing a mixture of $C_3$-$C_6$ olefins along with hydrogen gas, and (iii-b) an aromatization process in which at least a portion of said total $C_3$-$C_6$ paraffin fraction is contacted with a ZSM-5 zeolite catalyst at a temperature of at least 400° C. and up to 600° C. to form an aromatic fraction and hydrogen gas; and (iv) subjecting the $C_7^+$ partially unsaturated fraction, produced in the step (ii) oligomerization process, to a hydrogenation process by contacting the $C_7^+$ partially unsaturated fraction with a precious metal-containing hydrogenation catalyst in the presence of hydrogen gas produced by either or both of processes (iii-a) and (iii-b) at a temperature of at least 100° C. and up to 300° C. to produce the jet-diesel hydrocarbon fraction, wherein the jet-diesel hydrocarbon fraction contains a $C_8^+$ paraffin fraction with substantially no olefin or aromatic fraction.

BRIEF DESCRIPTION OF THE DRAWINGS

FIGS. 2A-2B. Comparison of the results of ethanol conversion over conventional 3D ZSM-5 (70) and 2D Pillared MFI (2D PMFI). FIG. 2A is a plot of the product distributions while

DETAILED DESCRIPTION OF THE INVENTION

The alcohol starting material considered herein is generally of the formula R—OH, where R is typically a straight-chained or branched alkyl group having at least one or two carbon atoms and up to any number of carbon atoms, e.g., up to three, four, five, or six carbon atoms, but more typically, up to three or four carbon atoms. In some embodiments, the alcohol contains one to four (1-4) or two to four (2-4) carbon atoms. The alcohol is typically a primary or secondary alcohol. Some examples of suitable alcohols include methanol, ethanol, n-propanol, isopropanol, n-butanol, isobutanol, sec-butanol, tert-butanol, n-pentanol, isopentanol, n-hexanol, isohexanol, n-heptanol, 2-ethylhexanol, and n-octanol. In some embodiments, the alcohol starting material contains at least methanol or ethanol, or methanol and/or ethanol in combination with one or more of the alcohols provided above, or an absence of any one or more alcohols other than methanol or ethanol, such as an absence of any one or more of the alcohols provided above other than methanol or ethanol. In some embodiments, the alcohol does not include methanol. The alcohol may or may not also be or include a diol, such as ethylene glycol or propylene glycol. The term "alcohol," as used herein, may refer to a single alcohol or a mixture (e.g., two, three, or more) of alcohols.

The alcohol can be in any concentration, including pure (dry) alcohol, i.e., at or about 100% or in aqueous solution when used in the presently described method. In some embodiments, the alcohol is a bio-alcohol, i.e., an alcohol that can be produced by a fermentation process. Most notable examples of bio-alcohols considered herein include ethanol, n-butanol (i.e., butanol), and isobutanol, as commonly found in fermentation streams. In particular embodiments, the alcohol is an aqueous solution of alcohol (i.e., the alcohol is a component of an aqueous solution), such as found in fermentation streams. In fermentation streams, the alcohol is typically in a concentration of no more than about 20% (vol/vol), 15%, 10%, or 5%, wherein the term "about" generally indicates within ±0.5%, 1%, 2%, 5%, or up to ±10% of the indicated value. The aqueous solution of alcohol may contain the alcohol in any of the foregoing amounts. In some embodiments, a fermentation stream or other alcoholic aqueous solution is directly contacted with the catalyst (typically, after filtration to remove solids) to effect the conversion of the alcohol in the fermentation stream. In other embodiments, the fermentation stream or other alcoholic aqueous solution is concentrated in alcohol (for example, of at least or up to 20%, 30%, 40%, or 50%) before contacting the fermentation stream with the catalyst. In yet other embodiments, alcohol in the fermentation stream or other alcoholic aqueous solution is selectively removed from the alcoholic aqueous solution, such as by distillation, to produce a substantially pure form of alcohol as the feedstock (e.g., a concentration of at least 90% or 95% of alcohol). In still other embodiments, the alcohol is completely dewatered into 100% alcohol before contacting with the catalyst.

In a first step (i.e., step (i)) of the method, the alcohol is contacted with a pillared two-dimensional zeolite catalyst having an MFI structure at a suitable elevated temperature, as further to discussed below, to result in conversion of the alcohol to hydrocarbons. Pillared two-dimensional zeolite catalysts having an MFI structure are well known in the art, as evidenced by, for example, Na et al., *J. Am. Chem. Soc.*, 2010, 132, 4169-4177, the contents of which are incorporated herein by reference. As discussed in detail in Na et al., the two-dimensional zeolite catalyst is prepared by synthesizing a multilamellar MFI zeolite using a zeolite-structure directing agent (SDA), such as $C_{22}H_{45}$—$N^+(CH_3)_2$—$C_6H_{12}$—$N^+(CH_3)_2$—$C_6H_{13}$, and pillaring of the zeolite with a silane, such as tetraethoxysilane, prior to SDA removal. The resulting MFI zeolite nanosheets are known to possess a mesoporous-microporous hierarchical structure, with mesopores having substantially uniform diameters in the interlamellar space. Generally, the pillared two-dimensional zeolite catalyst has a silicon to aluminum ratio of at least or above 30, 35, 40, 45, 50, 55, or 60. Step (i) typically employs a temperature of at least 200° C. and up to 500° C. In different embodiments, step (i) employs a temperature of precisely or about, for example, 200° C., 250° C., 300° C., 350° C., 400° C., 450° C., or 500° C., or a temperature within a range bounded by any two of the foregoing values, e.g., 200-500° C., 250-500° C., 300-500° C., 350-500° C., 400-500° C., 200-450° C., 250-450° C., 300-450° C., 350-450° C., 400-450° C., 200-400° C., 250-400° C., 300-400° C., 350-400° C., 200-350° C., 250-350° C., 300-350° C., 200-300° C., or 250-300° C. Generally, ambient (i.e., normal atmospheric) pressure of about 1 atm is used in step (i). However, in some embodiments, an elevated pressure may be used. For example, in some embodiments, the pressure may be elevated to, for example, 1.5, 2, 3, 4, or 5 atm. Notably, by virtue of the pillared catalyst and other conditions employed in step (i), the conversion of the alcohol is energy neutral or exothermic in step (i).

Generally, step (i) converts the alcohol to a mixture of hydrocarbons. The mixture of hydrocarbons generally includes: (a) a mixed olefin fraction containing a mixture of $C_2$-$C_5$ olefins; (b) a paraffin fraction containing $C_3$-$C_5$ paraffins; and (c) a gasoline fraction containing $C_6^+$ hydrocarbons. The mixed olefin fraction generally accounts for at least 25, 30, 35, or 40 carbon mol % of total fractions (a)-(c). Notably, as further discussed below, fractions (a) and (b) are also herein referred to as "a first mix olefin fraction" and "a first paraffin fraction", respectively, to distinguish the foregoing fractions from second or third fractions of similar or overlapping composition, as produced in subsequent steps, if desired.

The first mixed olefin fraction (i.e., containing a mixture of $C_2$-$C_5$ olefins), produced in step (i), may include or exclusively contain linear, branched, or cyclic alkenes containing two to five carbon atoms and one or two carbon-carbon double bonds. An example of a $C_2$ olefin is ethylene (ethene). An example of a $C_3$ olefin is propylene (propene). Some examples of $C_4$ olefins include 1-butene, cis-2-butene, trans-2-butene, isobutylene (2-methyl-propene), and 1,3-butadiene. Some examples of $C_5$ olefins include 1-pentene, cis-2-pentene, trans-2-pentene, 2-methyl-1-butene, 3-methyl-1-butene, 2-methyl-1,3-butadiene, and cyclopentene. Generally, the mixture of $C_2$-$C_5$ olefins contains ethylene in an amount of no more than 75, 80, 85, or 90 carbon mol % of the mixture of $C_2$-$C_5$ olefins.

The first paraffin fraction (i.e., containing $C_3$-$C_5$ paraffins) may include or exclusively contain linear, branched, or cyclic alkanes containing three to five carbon atoms. An example of a $C_3$ paraffin is propane. Some examples of $C_4$ paraffins include n-butane and tert-butane (2-methypropane). Some examples of $C_5$ paraffins include n-pentane, isopentane (3-methylbutane), and neopentane.

The gasoline fraction containing $C_6^+$ hydrocarbons substantially corresponds (e.g., in composition and/or properties) to the fractional distillate of petroleum commonly known as gasoline. The gasoline fraction typically includes $C_6^+$ hydrocarbons, i.e., hydrocarbons containing at least six carbon atoms. A small portion of $C_4$ or $C_5$ hydrocarbons may or may not be present, and hydrocarbons containing less than four or five carbon atoms are generally not present. The gasoline fraction more typically contains hydrocarbons containing 4-12, 5-12, or 6-12 carbon atoms. The gasoline fraction generally includes a mixture of linear, branched, and cyclic alkenes and alkanes, along with aromatic hydrocarbons. In some embodiments, the gasoline fraction contains no more than (up to) or less than 20, 25, 30, 35, or 40 carbon mol % aromatics, which is generally lower in aromatic content than conventional gasoline. Some examples of alkenes in the gasoline fraction include 1-hexene, cis-2-hexene, trans-2-hexene, cis-3-hexene, trans-3-hexene, 3-methyl-2-pentene, 4-methyl-2-pentene, 1-heptene, cis-2-heptene, trans-2-heptene, cis-3-heptene, trans-3-heptene, 1,3-heptadiene, 4-methyl-1-hexene, 1-octene, cis-2-octene, trans-2-octene, 2,4,4-trimethyl-1-pentene, 1,5-dimethylcyclopentene, ethylidenecyclopentane, cyclohexene, methylenecyclohexane, 1,4-dimethyl-1-cyclohexene, 1,2,3-trimethylcyclopentene, and cycloheptatriene. Some examples of alkanes in the gasoline fraction include n-hexane, isohexane, 2-methylpentane, 3-methylpentane, 2,2-dimethylbutane, n-heptane, isoheptane, 3-methyl-hexane, 2,2-dimethylpentane, 2,2,3-trimethylbutane, n-octane, 2,2,4-trimethylpentane (isooctane), 2-methylheptane, 1-nonane, isononane, 1-decane, isodecane, cyclohexane, methylcyclopentane, 1,2-dimethylcyclohexane, and cycloheptane. Some examples of aromatic compounds include benzene, toluene, o-xylene, p-xylene, 3,4-dimethylstyrene, ethylbenzene, 1-ethyl-4-methylbenzene, 1,3-dimethylbenzene, trimethylbenzenes (e.g., 1,3,5-trimethylbenzene), 1,3-diethylbenzene, isopropylbenzene, naphthalene, 1-methylnaphthalene, indane, and 4-methylindane.

At the completion of or during the alcohol conversion in step (i), hydrocarbon fractions (a) and (b) are separated from hydrocarbon fraction (c) by means well known in the art. Separation of (a) and (b) can be achieved by, for example, conventional distillation, as well known in the art. Fraction (c), the gasoline fraction, can advantageously be used as gasoline with a low aromatics content. Fractions (a) and (b), the mixed olefins and paraffin fractions, respectively, can be used for manufacturing other hydrocarbon fractions, as further discussed below. Notably, as other mixed olefin and paraffin fractions are produced subsequently in the process, the mixed olefins and paraffin fractions produced in step (i) are herein also referred to as the "first mixed olefin fraction" and "first paraffin fraction".

In step (ii) of the process, the first mixed olefin fraction, as produced in step (i), is subjected to an oligomerization process to result in a second paraffin fraction containing $C_3$-$C_6$ paraffins along with a $C_7^+$ partially unsaturated (oligomeric) fraction containing partially unsaturated hydrocarbons possessing at least seven carbon atoms. As well known in the art, the term "oligomerization" refers to a process of olefin coupling (vinyl addition), wherein the process typically includes at least one of dimerization, trimerization, and higher oligomerization, and/or dehydrocyclization. The second paraffin fraction, as produced by the oligomerization process, includes any of the $C_3$-$C_5$ paraffin compounds already described above for the $C_3$-$C_5$ paraffin fraction produced in step (i), and further includes $C_6$ paraffins (for example, n-hexane, isohexane, 2-methylpentane, 3-methylpentane, and/or 2,2-dimethylbutane). The oligomeric fraction contains alkenes with less unsaturation (fewer carbon-carbon double bonds) than present in the first mixed olefin fraction. The hydrocarbons in the oligomeric fraction typically possess up to 10, 12, or 14 carbon atoms (e.g., $C_{7-10}$, $C_{7-12}$, or $C_{7-14}$ partially unsaturated hydrocarbons).

The oligomerization process in step (ii) more specifically entails contacting the first mixed olefin fraction with an oligomerization catalyst at a temperature of at least 40° C. and up to 300° C. In different embodiments, step (ii) employs a temperature of precisely or about, for example, 40° C., 50° C., 60° C., 70° C., 80° C., 90° C., 100° C., 150° C., 200° C., 250° C., or 300° C., or a temperature within a range bounded by any two of the foregoing values, e.g., 40-300° C., 40-250° C., 40-200° C., 40-150° C., 50-300° C., 50-250° C., 50-200° C., 50-150° C., 80-300° C., 80-250° C., 80-200° C., or 80-150° C. Oligomerization catalysts are well known in the art, as evidenced in, for example, A. Lacarriere et al., ChemSusChem, 5, 1787-1792 (2012), the contents of which are herein incorporated by reference. As well known, oligomerization catalysts can be divided into two main categories: acid catalysts, particularly suited for the oligomerization of $C_3$ or higher olefins, and nickel-containing catalysts (e.g., nickel complexes or nickel-exchanged zeolite), particularly suited for ethylene oligomerization. Some examples of oligomerization catalysts include acid zeolite catalysts (e.g., H-BEA, H-ZSM-5, MCM-41, H-ZSM-22, or H-ZSM-57), metal-containing zeolite catalysts (e.g., nickeland aluminum-exchanged zeolites, such as NiMCM-41, AlMCM-41, NiMCM-48, and AlMCM-48), amorphous aluminosilicate, sulfonic acid ion-exchange resins (e.g., Amberlyst® 15, Amberlyst® 35, Amberlyst® 36, Purolite®, Dowex®, Lewatit®), sulfated alumina, and solid phosphoric acid. The oligomerization process may employ standard pressure (about 1 atm) or an elevated pressure (e.g., at least or above 10, 20, 30, or 50 atm). The oligomerization process may be conducted under an inert gas atmosphere. At the completion of or during the oligomerization process in step (ii), the second paraffin fraction and $C_7^+$ partially unsaturated (oligomeric) fraction are separated from each other by means well known in the art, and the first and second paraffin fractions are combined to result in a total $C_3$-$C_6$ paraffin fraction.

In step (iii) of the process, at least a portion (or all) of the total $C_3$-$C_6$ paraffin fraction, as produced in step (ii), is subjected to at least one of the following processes: (iii-a) a dehydrogenation process in which at least a portion of the total $C_3$-$C_6$ paraffin fraction is contacted with a dehydrogenation catalyst at a temperature of at least 500° C. and up to 600° C. to form a second mixed olefin fraction containing a mixture of $C_3$-$C_6$ olefins along with hydrogen gas, and (iii-b) an aromatization process in which at least a portion of the total $C_3$-$C_6$ paraffin fraction is contacted with a ZSM-5 zeolite catalyst at a temperature of at least 400° C. and up to 600° C. to form an aromatic fraction and hydrogen gas. In a first embodiment, at least a portion (or all) of the total $C_3$-$C_6$ paraffin fraction, as produced in step (ii), is subjected to only process (iii-a) and not process (iii-b). In a second embodiment, at least a portion (or all) of the total $C_3$-$C_6$ paraffin fraction, as produced in step (ii), is subjected to only process (iii-b) and not process (iii-a). In a third embodiment, a first portion of the total $C_3$-$C_6$ paraffin fraction is subjected to step (iii-a) and a second portion of the total $C_3$-$C_6$ paraffin fraction is separately subjected to step (iii-b). The term "at least a portion" may independently mean precisely, at least, more than, up to, or less than, for example, 10, 20, 30, 40, 50, 60, 70, 80, 90, or 95%, or up to or less than 100%, independently for steps (iii-a) and (iii-b).

Step (iii-a), if used, employs a dehydrogenation catalyst to convert at least a portion of the total $C_3$-$C_6$ paraffin fraction to the second mixed olefin fraction containing a mixture of $C_3$-$C_6$ olefins along with hydrogen gas. Dehydrogenation catalysts are well known in the art, as evidenced by, for example, Z. Nawaz, Reviews in Chemical Engineering, 31(5), 2015, the contents of which are herein incorporated by reference. In particular embodiments, the dehydrogenation catalyst is a noble metal-containing (e.g., Pt-based) or metal oxide-containing (e.g., Cr oxide-based) catalyst. In some embodiments, the dehydrogenation catalyst may be an oxide catalyst (e.g., $Al_2O_3$, $TiO_2$, $CeO_2$, or $ZrO_2$) coated or impregnated with platinum (Pt), nickel (Ni), rhodium (Rh), ruthenium (Ru) or other noble metal or precious metal. Step (iii-a) employs a temperature of at least 500° C. and up to 600° C., or a temperature within a sub-range thereof, e.g., precisely or about 520° C., 550° C., or 580° C., or a range between any of the foregoing values, e.g., 520° C.-600° C., 500° C.-580° C., 520° C.-580° C., 550° C.-600° C., 500° C.-550° C., 520° C.-550° C., or 550° C.-580° C. Step (iii-a) may employ standard pressure (about 1 atm) or an elevated pressure (e.g., at least or above 10, 20, 30, or 50 atm), and may be conducted under a standard air atmosphere or an inert gas (e.g., nitrogen or argon) atmosphere. The second mixed olefin fraction produced in step (iii-a) contains a mixture of $C_3$-$C_6$ olefins along with hydrogen gas as a byproduct. The second mixed olefin fraction includes any of the $C_3$-$C_5$ olefin compounds already described above for the first mixed olefin fraction produced in step (i), and further includes $C_6$ olefins, e.g., for example, 1-hexene, 2-hexene, 3-hexene, 4-methyl-1-pentene, 3-methyl-1-pentene, 2-methyl-1-pentene, 4-methyl-2-pentene (cis or trans), 3-methyl-2-pentene (cis or trans), 2-methyl-2-pentene, 2,3-dimethyl-1-butene, 2,3-dimethyl-2-butene, and/or 2,3-dimethyl-1,3-butadiene.

Step (iii-b), if used, employs a ZSM-5 zeolite (aromatization) catalyst to convert at least a portion of the total $C_3$-$C_6$ paraffin fraction to an aromatic fraction and hydrogen gas. Such catalysts are well known in the art, as evidenced by, for example, Y. Xiang et al., *Catalysis Science & Technology*, 8, 1500-1516, 2018 and A Bhan et al., *Catalysis Reviews: Science and Engineering*, 50:1, 19-151, DOI:10.1080/01614940701804745, the contents of which are herein incorporated by reference. In particular embodiments, the aromatization catalyst is non-metallized ZSM-5 (e.g., HZSM-5) or a metalized (e.g., gallium-, zinc-, copper-, or platinum-modified or bimetallic) ZSM-5 catalyst. Step (iii-b) employs a temperature of at least 400° C. and up to 600° C., or a temperature within a sub-range thereof, e.g., precisely or about 420° C., 450° C., 480° C., 500° C., 520° C., 550° C., or 580° C., or a range between any of the foregoing values, e.g., 420° C.-600° C., 400° C.-580° C., 420° C.-580° C., 450° C.-600° C., 400° C.-550° C., 420° C.-550° C., or 450° C.-580° C., or any of the temperature ranges provided in step (iii-a). Step (iii-b) may employ standard pressure (about 1 atm) or an elevated pressure (e.g., at least or above 1, 2, 5, 10, 20, 30, 40, or 50 atm, or a range therein, e.g., 1-5 atm, 2-5 atm, 1-10 atm, or 2-10 atm), and may be conducted under a standard air atmosphere or an inert gas (e.g., nitrogen or argon) atmosphere. The aromatic fraction produced in step (iii-b) contains a mixture of aromatic compounds along with hydrogen gas as a byproduct. The aromatic compounds may include, for example, any of the aromatic compounds described above in the gasoline fraction produced in step (i).

In step (iv) of the process, the $C_7^+$ partially unsaturated (oligomeric) fraction, produced in the step (ii) oligomerization process, is subjected to a hydrogenation process by contacting the oligomeric fraction with a precious metal-containing hydrogenation catalyst in the presence of hydrogen gas produced by either or both of processes (iii-a) and (iii-b) at a temperature of at least 100° C., 150° C., or 200° C. and up to 250° C. or 300° C. to produce the jet-diesel hydrocarbon fraction. The jet-diesel hydrocarbon fraction contains a $C_8^+$ paraffin fraction with substantially no olefin or aromatic fraction. Precious metal-containing hydrogenation catalysts are well known in the art, e.g., Pt or Pd on an oxide support, such as alumina ($Al_2O_3$). Step (iv) may employ standard pressure (about 1 atm) or an elevated pressure (e.g., at least or above 1, 2, 5, 10, 20, 30, 40, or 50 atm, or a range therein, e.g., 1-5 atm, 2-5 atm, 1-10 atm, 2-10 atm, 1-30 atm, or 2-30 atm), and may be conducted under a standard air atmosphere or an inert gas (e.g., nitrogen or argon) atmosphere. The $C_8^+$ paraffin fraction in the jet-diesel hydrocarbon fraction includes or exclusively contains alkanes having at least eight, nine, or ten carbon atoms and up to twelve, fourteen, sixteen, eighteen, or twenty carbon atoms, e.g., a range of $C_8$-$C_{20}$, $C_8$-$C_{18}$, $C_8$-$C_{16}$, $C_8$-$C_{14}$, $C_9$-$C_{20}$, $C_9$-$C_{18}$, $C_9$-$C_{16}$, $C_9$-$C_{14}$, $C_{10}$-$C_{20}$, $C_{10}$-$C_{18}$, $C_{10}$-$C_{16}$, or $C_{10}$-$C_{14}$ alkanes. In different embodiments, the hydrogen gas produced by one or both of processes (iii-a) and (iii-b) provides at least or more than 20%, 30%, 40%, 50%, 60%, 70%, 75%, 80%, 85%, 90%, or 95% of the hydrogen required for completion of the hydrogenation process in step (iv). In another embodiment, the hydrogen gas produced by one or both of processes (iii-a) and (iii-b) provides all of the hydrogen required for completion of the hydrogenation process in step (iv).

For any of the process steps, the catalyst and reactor can have any of the designs known in the art for catalytically treating a fluid or gas at elevated temperatures, such as a fluidized bed reactor. Moreover, the process may be in a continuous or batch mode. For step (i), the alcohol is typically injected into a heated reactor such that the alcohol is quickly volatilized into vapor form, and the vapor passed over the catalyst. In some embodiments, the reactor design includes a boiler unit and a reactor unit if a fermentation stream is used directly as a feedstock without purification. The boiler unit is generally not needed if a fermentation stream is distilled to concentrate ethanol because the distillation process removes the dissolved solids in the fermentation streams. The boiler unit volatilizes liquid feedstock into gases prior to entry into the reactor unit and withholds dissolved solids.

In an alternative embodiment of the method, the first or second mixed olefin fraction, such as produced in step (i) or (iii), may be converted to a synthetic fossil fuel, fuel additive, or commodity chemical. The term "synthetic fossil fuel" refers to a mixture of hydrocarbon compounds useful as a fuel or as a blendstock in a fuel. The mixture of hydrocarbon compounds substantially corresponds (e.g., in composition and/or properties) to a known petrochemical fuel, such as petroleum, or a fractional distillate of petroleum. Some examples of petrochemical fuels include jet fuel (i.e., jet propellant, such as JP-8), gasoline, kerosene, and diesel. Like hydrocarbon fuel grades in current use, the mixture of hydrocarbon compounds in the synthetic fossil fuel can be predominantly or exclusively composed of alkanes, alkenes, aromatics, or a mixture thereof. Although aromatics (particularly benzene) may be present in the hydrocarbon mixture, their presence may be minimized to adhere to current fuel standards. The raw hydrocarbon product may also be fractionated by distillation into different fuel grades, each of which is known to be within a certain boiling point range. A particular advantage of the presently described method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the catalyst (e.g., catalytic metal), amount of catalyst (e.g., ratio of catalyst to alcohol precursor), processing temperature, and flow rate (e.g., weight hourly space velocity, WHSV).

In some embodiments, the conversion method described above is integrated with a fermentation process, wherein the fermentation process produces the alcohol used as feedstock for the conversion process. By being "integrated" is meant that alcohol produced at a fermentation facility or zone is sent to and processed at a conversion facility or zone that performs the conversion process described above. Preferably, in order to minimize production costs, the fermentation process is in close enough proximity to the conversion facility or zone, or includes appropriate conduits for transferring produced alcohol to the conversion facility or zone, thereby not requiring the alcohol to be shipped. In particular embodiments, the fermentation stream produced in the fermentation facility is directly transferred to the conversion facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermentation facility to produce alcohol. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass generally refers to lignocellulosic matter (i.e., plant material), such as wood, grass, leaves, paper, corn husks, sugar cane, bagasse, and nut hulls. Generally, biomass-to-ethanol conversion is performed by 1) pretreating biomass under well-known conditions to loosen lignin and hemicellulosic material from cellulosic material, 2) breaking down cellulosic material into fermentable saccharide material by the action of a cellulase enzyme, and 3) fermentation of the saccharide material, typically by the action of a fermenting organism, such as suitable yeast, to produce one or more alcohols.

In other embodiments, the alcohol is produced from a more direct sugar source, such as a plant-based source of sugars, such as sugar cane or a grain starch (such as corn starch). Ethanol production via corn starch (i.e., corn starch ethanol) and via sugar cane (i.e., cane sugar ethanol) currently represent some of the largest commercial production methods of ethanol. Integration of the instant conversion process with any of these large scale ethanol production methods is contemplated herein.

Examples have been set forth below for the purpose of illustration and to describe certain specific embodiments of the invention. However, the scope of this invention is not to be in any way limited by the examples set forth herein.

Example 1

Pillared H-MFI Catalyst and 3D ZSM-5 for Ethanol Conversion to Olefins and Gasoline Fraction Synthesis of pillared H-MFI. The synthetic procedure described in Na et al. (J. Am. Chem. Soc. 2010, 132, 4169-4177) was used for producing the pillared MFI catalyst. The final pillared H-MFI composition (as gel) had a Si/Al ratio of 70.

Catalytic Test. The reaction was conducted in a tubular fixed-bed quartz reactor in a vertical tubular furnace. Typically, 0.15 g of catalyst was treated in situ by heating it at 5K min$^{-1}$ to 673 K and holding at 673 K under He flow (15 ccm) for 30 minutes to remove adsorbed species before measuring catalytic performance. The flow rate of He was set using a mass flow controller. Ethanol was fed by syringe pumps and was evaporated inside the ⅛-inch stainless steel transfer lines. The types and concentrations of reactants and products in the stream were measured by a gas-chromatograph with thermal conductivity detector (TCD) and a flame ionization detector (FID). A gas chromatograph mass-spectrometer (GC-MS) was used to determine the peak position of reactants and products. The results are summarized in Table 1 below. Ethanol conversion over conventional 3D ZSM-5 (Si/Al ratio of 70) was also tested for ethanol conversion under the same conditions.

TABLE 1

Catalyst performance of pillared H-MFI (70) for ethanol conversion to mixed olefins

| Temp (K) | Conversion | Ethylene Sel (%) | Propene Sel (%) | Butenes Sel (%) | $C_5$ olefins Sel (%) | $C_2$-$C_5$ total olefins Sel (%) | $C_{6+}$ Sel (Gasoline) (%) | Oxygenate Sel (%) | $C_1$-$C_5$ Paraffin Sel (%) |
|---|---|---|---|---|---|---|---|---|---|
| 573 | 100 | 77.6 | 3.6 | 6.6 | 3.1 | 90.9 | 3.8 | 2.0 | 3.3 |
| 623 | 100 | 63.9 | 7.9 | 10.7 | 4.4 | 86.9 | 6.7 | 1.9 | 3.2 |
| 673 | 100 | 37.9 | 14.8 | 17.3 | 6.6 | 76.6 | 9.7 | 3.5 | 10.2 |
| 723 | 100 | 47.2 | 18.9 | 15.4 | 6.0 | 87.5 | 5.1 | 1.3 | 4.3 |

Figure 2A:
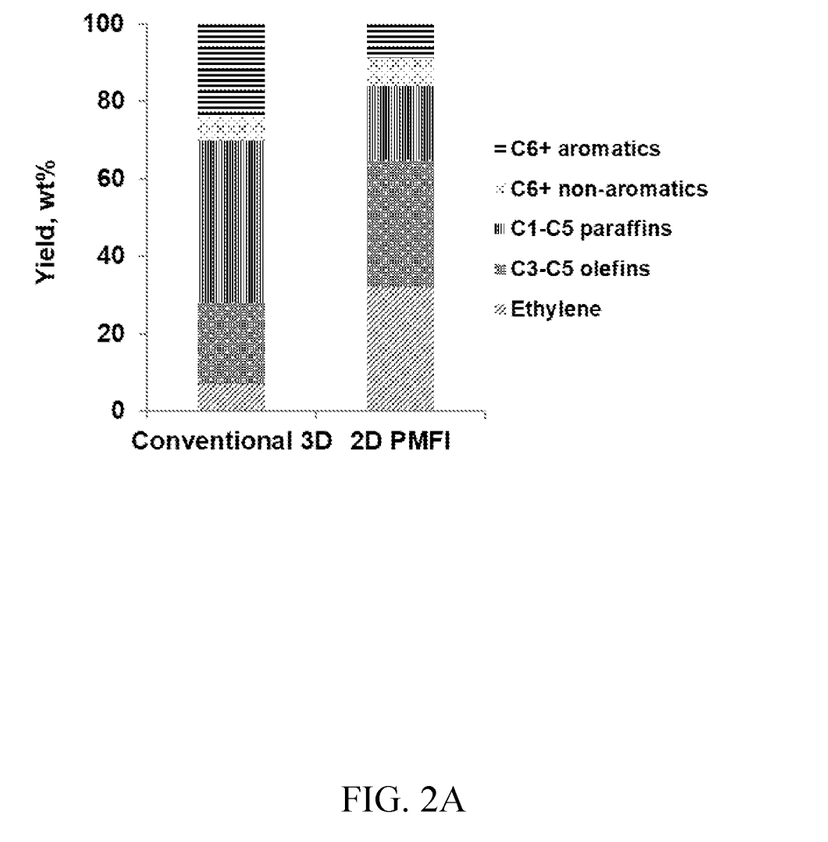
Figure 2B:
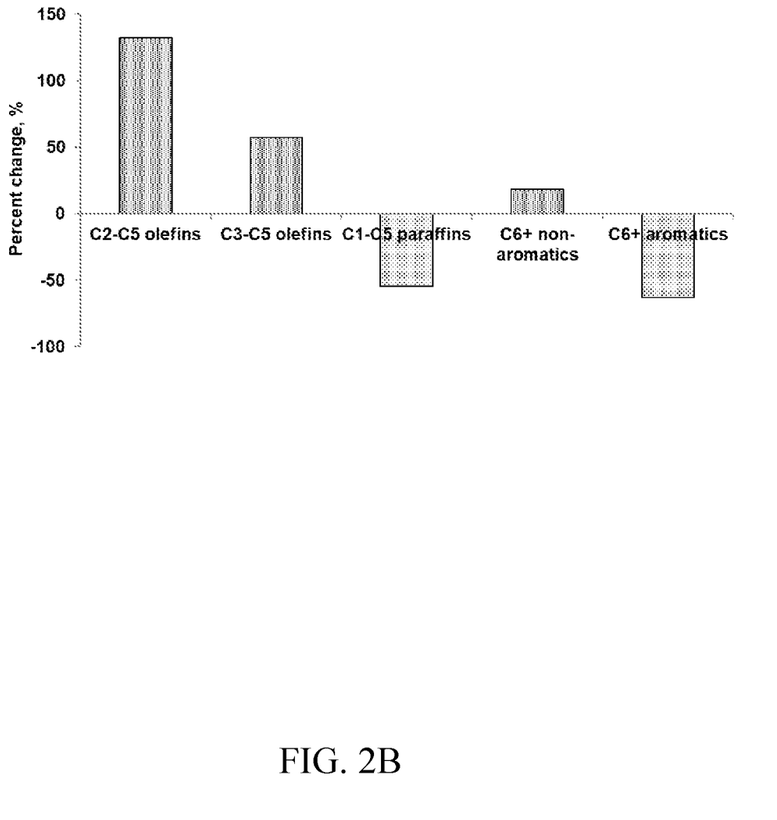
FIG. 2B is a plot of the percent changes of products when comparing 2D with 3D MFI. The conditions include the following: 673 K, ambient pressure, and 1.6 h$^{-1}$ space velocity.

FIGS. 2A and 2B compare results of ethanol conversion over conventional 3D ZSM-5 (70) and 2D Pillared MFI (2D PMFI). FIG. 2A plots the product distributions while FIG. 2B plots the percent changes of products when comparing 2D with 3D MFI. The conditions include the following: 673 K, ambient pressure, and 1.6 h$^{-1}$ space velocity. As shown in FIG. 2A, conventional 3D H-ZSM-5 produced a significant amount of light $C_1$-$C_5$ paraffins and $C_{6+}$ aromatics, which is undesirable for jet-diesel fuel applications. In comparison, the 2D PMFI catalyst produced 55% less $C_1$-$C_5$ paraffins and 63% less $C_{6+}$ aromatics (FIG. 2B), and with $C_2$-$C_5$ olefins selectivity dramatically promoted, favoring a high yield of jet-diesel range hydrocarbons.

Amberlyst® 36 Catalyst for Oligomerization of C3-C6 Mixed Olefins

Catalytic Test. Amberlyst® 36 (a bead-form, macroporous, sulfonic acid resin) was dried at 383 K in the oven under air flow for 3 hours, followed by vacuum drying at 373 K for 5 hours. The oligomerization experiments were performed in a Parr batch reactor. The dried catalyst and Parr reactor were cooled down to 243 K for 1 hour in preparation for introducing olefins. Simulated mixed olefins (propene, butenes, pentenes, hexenes) were introduced into the cooled batch reactor in liquid form. Dried Amberlyst® 36 was added into the Parr reactor followed by tightening the reactor. Then propylene (10% in nitrogen) was introduced to the reactor after purging with nitrogen gas three times. The Parr reactor was pressurized to 40 bar and heated to 423 K and held for 3 to 9 hours and cooled down to 243 K. The products were weighed to calculate the mass balance. The products were analyzed by gas chromatography equipped with an FID detector. Product identification was performed by injecting samples into the gas chromatograph equipped with a mass spectrometer. $C_7$-$C_{40}$ hydrocarbon standards were also used to aid in product determination. The above example demonstrated oligomerization of $C_3$-$C_6$ olefins. Conversion of $C_2$-$C_6$ olefins can be achieved over Ni-modified MCM-41 and H-MCM-41, as demonstrated in ChemSusChem 2012, 5, 1787-1792. The product selectivities (wt. %) of oligomerization of $C_3$-$C_6$ mixed olefins are provided in Table 2 below.

TABLE 2

Example product selectivities (wt. %) of oligomerization of $C_3$-$C_6$ mixed olefins over Amberlyst-36 catalyst$^a$

| C4 | C5 | C6 | C7 | C8 | C9 | C10 | C11 | C12 | C13 | C14 | C15 | C16 | C17-21 | C22+ |
|---|---|---|---|---|---|---|---|---|---|---|---|---|---|---|
| 7.6 | 6.3 | 5.1 | 9.4 | 16.5 | 12.9 | 18.5 | 10.9 | 5.5 | 2.5 | 1.5 | 0.9 | 0.9 | 1.2 | 0.4 |

$^a$423 K, 40 bar, mass balance 94-98%

Table 3, below, provides an estimation of hydrogen generated from step iii-b and hydrogen needed for the hydrogenation step in step iv, as shown in FIG. 1. Notably, as shown in Table 3, internally generated hydrogen during aromatics formation is generally sufficient for hydrogenation in step iv.

TABLE 3

Estimated hydrogen generated from step iii-b and hydrogen needed for step iv hydrogenation step

| Ethanol, | Paraffins, mol C [a] | | | Ratio of aromatics (carbon) [b] | | | Conversion of paraffins to BTX in step 3b, % | Amount of $H_2$ generated from step 3b, mol | $C_2$-$C_5$ olefins (carbon), mol [a] | Olefin conversion to olefin oligomers in step 2 | Amount of $H_2$ need in step 4 [c] | | | |
|---|---|---|---|---|---|---|---|---|---|---|---|---|---|---|
| mol C | $C_3$ | $C_4$ | $C_5$ | Benzene | Toluene | xylene | | | | | $C_9H_{20}$ | $C_{10}H_{22}$ | $C_{11}H_{24}$ | $C_{12}H_{26}$ |
| 100 | 2.5 | 12.7 | 1.7 | 2 | 6 | 8 | 80 | 9.1 | 66.1 | 95.0 | 7.0 | 6.3 | 5.7 | 5.2 |
| | | | | | | | 70 | 7.9 | | 90.0 | 6.6 | 5.9 | 5.4 | 5.0 |
| | | | | | | | 60 | 6.8 | | 85.0 | 6.2 | 5.6 | 5.1 | 4.7 |

[a] Ethanol conversion conditions: 673 K, ambient pressure, 1.6$^{-1}$ space velocity;
[b] In step iii-b, assuming benzene, toluene, and xylene carbon ratio 2:6:8.
[c] In the final liquid hydrocarbon fuels, four different average molecular formulas were assumed.

While there have been shown and described what are at present considered the preferred embodiments of the invention, those skilled in the art may make various changes and modifications which remain within the scope of the invention defined by the appended claims.

What is claimed is:

1. A method for converting an alcohol to a mixture of hydrocarbons, the method comprising contacting a reactant source comprising the alcohol with a pillared two-dimensional zeolite catalyst having an MFI structure at a temperature of at least 200° C. and up to 500° C. to result in conversion of said alcohol to said hydrocarbons, wherein said hydrocarbons comprise: (a) a mixed olefin fraction containing a mixture of $C_2$-$C_5$ olefins; (b) a paraffin fraction containing $C_3$-$C_5$ paraffins; and (c) a gasoline fraction containing $C_6^+$ hydrocarbons; wherein the mixed olefin fraction accounts for at least 25 carbon mol % of total fractions, and the conversion of the alcohol is energy neutral or exothermic, wherein the alcohol has the formula R—OH where R is a straight-chained or branched alkyl group, and said alcohol is the only reactant present in the reactant source that can undergo conversion to the mixture of hydrocarbons.

2. The method of claim 1, wherein said alcohol contains two to four carbon atoms.

3. The method of claim 1, wherein said alcohol comprises ethanol.

4. The method of claim 1, wherein said temperature is at least 300° C. and up to 500° C.

5. The method of claim 1, wherein said mixture of $C_2$-$C_5$ olefins contains ethylene in an amount of no more than 85 carbon mol % of said mixture of $C_2$-$C_5$ olefins.

6. The method of claim 1, wherein said mixed olefin fraction accounts for at least 30 carbon mol % of total fractions.

7. The method of claim 1, wherein said gasoline fraction contains no more than 30 carbon mol % aromatics.

8. The method of claim 1, wherein said pillared two-dimensional zeolite catalyst has a silicon to aluminum ratio of at least 30.

9. A method for converting an alcohol to a jet-diesel hydrocarbon fraction, the method comprising:

(i) contacting the alcohol with a pillared two-dimensional zeolite catalyst having an MFI structure at a temperature of at least 200° C. and up to 500° C. to result in conversion of said alcohol to said hydrocarbons, wherein said hydrocarbons comprise: (a) a first mixed olefin fraction containing a mixture of $C_2$-$C_5$ olefins; (b) a first paraffin fraction containing $C_3$-$C_5$ paraffins; and (c) a gasoline fraction containing $C_6^+$ hydrocarbons; wherein the first mixed olefin fraction accounts for at least 25 carbon mol % of total fractions (a)-(c), and the conversion of the alcohol is energy neutral or exothermic;

(ii) subjecting said first mixed olefin fraction to an oligomerization process in which the first mixed olefin fraction is contacted with an oligomerization catalyst at a temperature of at least 40° C. and up to 300° C. to result in a second paraffin fraction containing $C_3$-$C_6$ paraffins along with a $C_7^+$ partially unsaturated fraction, and combining said first and second paraffin fractions to result in a total $C_3$-$C_6$ paraffin fraction;

(iii) subjecting at least a portion of said total $C_3$-$C_6$ paraffin fraction to one or both of the following processes: (iii-a) a dehydrogenation process in which at least a portion of said total $C_3$-$C_6$ paraffin fraction is contacted with a dehydrogenation catalyst at a temperature of at least 500° C. and up to 600° C. to form a second mixed olefin fraction containing a mixture of $C_3$-$C_6$ olefins along with hydrogen gas, and (iii-b) an aromatization process in which at least a portion of said total $C_3$-$C_6$ paraffin fraction is contacted with a ZSM-5 zeolite catalyst at a temperature of at least 400° C. and up to 600° C. to form an aromatic fraction and hydrogen gas; and (iv) subjecting the $C_7^+$ partially unsaturated fraction, produced in the step (ii) oligomerization process, to a hydrogenation process by contacting the $C_7^+$ partially unsaturated fraction with a precious metal-containing hydrogenation catalyst in the presence of hydrogen gas produced by either or both of processes (iii-a) and (iii-b) at a temperature of at least 100° C. and up to 300° C. to produce the jet-diesel hydrocarbon fraction, wherein the jet-diesel hydrocarbon fraction contains a $C_8^+$ paraffin fraction with substantially no olefin or aromatic fraction.

10. The method of claim 9, wherein said alcohol contains two to four carbon atoms.

11. The method of claim 9, wherein said alcohol comprises ethanol.

12. The method of claim 9, wherein the temperature in step (i) is at least 300° C. and up to 500° C.

13. The method of claim 9, wherein said mixture of $C_2$-$C_5$ olefins in the first mixed olefin fraction in step (i) contains ethylene in an amount of no more than 85 carbon mol % of said mixture of $C_2$-$C_5$ olefins.

14. The method of claim 9, wherein said first mixed olefin fraction in step (i) accounts for at least 30 carbon mol % of total fractions (a)-(c).

15. The method of claim 9, wherein said gasoline fraction in step (i) contains no more than 30 carbon mol % aromatics.

16. The method of claim 9, wherein said pillared two-dimensional zeolite catalyst in step (i) has a silicon to aluminum ratio of at least 30.

17. The method of claim 9, wherein step (iii) comprises subjecting at least a portion of said total $C_3$-$C_6$ paraffin fraction to the following process: (iii-a) a dehydrogenation process in which at least a portion of said total $C_3$-$C_6$ paraffin fraction is contacted with a dehydrogenation catalyst at a temperature of at least 500° C. and up to 600° C. to form a second mixed olefin fraction containing a mixture of $C_3$-$C_5$ olefins along with hydrogen gas.

18. The method of claim 9, wherein step (iii) comprises subjecting at least a portion of said total $C_3$-$C_6$ paraffin fraction to the following process: (iii-b) an aromatization process in which at least a portion of said total $C_3$-$C_6$ paraffin fraction is contacted with a ZSM-5 zeolite catalyst at a temperature of at least 400° C. and up to 600° C. to form an aromatic fraction and hydrogen gas.

19. The method of claim 9, wherein step (iii) comprises subjecting a first portion of said total $C_3$-$C_6$ paraffin fraction to step (iii-a) and a second portion of said total $C_3$-$C_6$ paraffin fraction to step (iii-b).

20. The method of claim 9, wherein the hydrogen gas produced by one or both of processes (iii-a) and (iii-b) provides at least 50% of the hydrogen required for completion of the hydrogenation process in step (iv).

21. The method of claim 9, wherein the hydrogen gas produced by one or both of processes (iii-a) and (iii-b) provides at least 75% of the hydrogen required for completion of the hydrogenation process in step (iv).

22. The method of claim 9, wherein the hydrogen gas produced by one or both of processes (iii-a) and (iii-b) provides all of the hydrogen required for completion of the hydrogenation process in step (iv).

* * * * *